(12) United States Patent
Hoerstrup et al.

(10) Patent No.: US 8,192,981 B2
(45) Date of Patent: Jun. 5, 2012

(54) BIOREACTOR SYSTEM

(75) Inventors: Simon P. Hoerstrup, Zürich (CH);
Gregor Zünd, Zürich (CH)

(73) Assignee: Universität Zürich, Zurich (CH)

( * ) Notice: Subject to any disclaimer, the term of this patent is extended or adjusted under 35 U.S.C. 154(b) by 80 days.

(21) Appl. No.: 12/085,494

(22) PCT Filed: Nov. 24, 2006

(86) PCT No.: PCT/EP2006/011304
§ 371 (c)(1),
(2), (4) Date: Oct. 30, 2009

(87) PCT Pub. No.: WO2007/059999
PCT Pub. Date: May 31, 2007

(65) Prior Publication Data
US 2010/0041132 A1   Feb. 18, 2010

(30) Foreign Application Priority Data

Nov. 24, 2005   (GB) .................................. 0523950.4

(51) Int. Cl.
*C12N 5/02* (2006.01)
*C12N 5/00* (2006.01)
*C12M 3/00* (2006.01)
*A61F 2/24* (2006.01)

(52) U.S. Cl. .................. 435/293.1; 435/289.1; 435/325; 435/395; 623/2.17

(58) Field of Classification Search ............... 435/293.1, 435/289.1, 325, 395; 623/2.17
See application file for complete search history.

(56) References Cited

FOREIGN PATENT DOCUMENTS

| WO | WO 03/001060 A1 | 1/2003 |
| WO | WO 03/080139 A2 | 10/2003 |

OTHER PUBLICATIONS

Abilez, Oscar, et al., "A Novel Culture System Shows that Stem Cells can be Grown in 3D and Under Physiologic Pulsatile Conditions for Tissue Engineering of Vascular Grafts," J. Surgical Research 132(2): 170-177 (May 2006).
Hildebrand, Daniel K., et al., "Design and Hydrodynamic Evaluation of a Novel Pulsatile Bioreactor for Biologically Active Heart Valves," Annals of Biomedical Engineering 32(8): 1039-49 (Aug. 2004).
Schenke-Layland, K., et al., "Complete Dynamic Repopulaton of Decellularized Heart Valves by Application of Defined Physical Signals—An In Vitro Study," Cardiovascular Research 60(3): 497-509 (Dec. 2003).

(Continued)

*Primary Examiner* — Nathan Bowers
*Assistant Examiner* — Gautam Prakash
(74) *Attorney, Agent, or Firm* — Sughrue Mion, PLLC

(57) ABSTRACT

In one aspect the invention provides a bioreactor system for the production of tissue prostheses. The system includes a bioreactor, a culture medium reservoir coupled to the bioreactor by a first conduit and a second conduit, a pump operable to pump fluid into and draw fluid out of a pumping chamber defined in the bioreactor to generate a pulsatile flow of culture medium through the reservoir and bioreactor via said first and second conduits, one or more flow meters operable to generate flow rate signals representative of the rate of culture medium flow through one or both of said first and second conduits, and a controller arranged to receive said flow rate signals from said one or more flow meters and to control the pump means in response to said received flow rate signals to provide a desired rate of culture medium flow.

14 Claims, 4 Drawing Sheets

OTHER PUBLICATIONS

Breuer CK, Shin'oka T, Tanel RE, Zund G, Mooney DJ, Ma PX, Miura T, Colan S, Langer R, Mayer JE, Vacanti JP. Tissue engineering lamb heart valve leaflets. Biotechnol Bioeng. Jun. 5, 1996;50(5):562-7.

Hill, Ronald J. et al., Quantitation of Types I and III Collagens in Human Tissue Samples and Cell Culture by Cyanogen Bromide Peptide Analysis, Analytical Biochemistry 141, 83-93 (1984).

Hoerstrup et al, Functional living Trileaflet Heart Valves Grown In Vitro., Circulation 2000; 102;44-49.

Hoerstrup SP, Sodian R, Sperling JS, Vacanti JP, Mayer JE Jr. New pulsatile bioreactor for in vitro formation of tissue engineered heart valves. Tissue Eng. Feb. 2000;6(1):75-9.

Hoerstrup SP, Zünd G, Ye Q, Schoeberlein A, Schmid AC, Turina MI. Tissue engineering of a bioprosthetic heart valve: stimulation of extracellular matrix assessed by hydroxyproline assay. ASAIO J. Sep.-Oct. 1999;45(5):397-402.

Hoerstrup, Simon P., et al, Functional Grown in Tissue-Engineered Living, Vascular Grats: Follow-Up at 100 Weeks in a Large Animal Model, Journal of American Heart Association; Circulations 2006; 114; 159-166.

Kanda K, Matsuda T. Behavior of arterial wall cells cultured on periodically stretched substrates. Cell Transplant. Nov.-Dec. 1993;2(6):475-84.

Mooney DJ, Breuer C, McNamara K, Vacanti JP, Langer R. Fabricating tubular devices from polymers of lactic and glycolic Acid for tissue engineering. Tissue Eng. 1995;1(2):107-18.

Mooney DJ, Organ G, Vacanti JP, Langer R. Design and fabrication of biodegradable polymer devices to engineer tubular tissues. Cell Transplant. Mar.-Apr. 1994;3(2):203-10.

Shinoka T, Breuer CK, Tanel RE, Zund G, Miura T, Ma PX, Langer R, Vacanti JP, Mayer JE Jr. Tissue engineering heart valves: valve leaflet replacement study in a lamb model. Ann Thorac Surg. Dec. 1995;60(6 Suppl):S513-6. presented 20.-22.4.1995 in Boston.

Shinoka T, Ma PX, Shum-Tim D, Breuer CK, Cusick RA, Zund G, Langer R, Vacanti JP, Mayer JE Jr. Tissue-engineered heart valves. Autologous valve leaflet replacement study in a lamb model. Circulation. Nov. 1, 1996;94(9 Suppl):II164-8.

Sodian, et al, Early in vivo experience with Tissue-Engineered Trileaflet Heart Valves, Circulation 2000; 102, 22-29.

Zünd et al; The in vitro construction of a tissue engineered bioprosthetic heart valve, European Journal of Cardio-Thoracic Surgery, 1997; 11:493-497; Presented Sep. 24-27, 1995 in Paris.

Zünd G, Hoerstrup SP, Schoeberlein A, Lachat M, Uhlschmid G, Vogt PR, Turina M. Tissue engineering: a new approach in cardiovascular surgery: Seeding of human fibroblasts followed by human endothelial cells on resorbable mesh. Eur J Cardiothorac Surg. Feb. 1998;13(2):160-4.

BIOREACTOR SYSTEM

CROSS-REFERENCE TO RELATED APPLICATIONS

This is a National Stage application of PCT International Application No. PCT/EP2006/011304, filed Nov. 24, 2006, which in turn claims the benefit pursuant to 35 U.S.C. §119(a) of GB Application No. 0523950.4, filed on Nov. 24, 2005 each of which are hereby incorporated by reference in its entirety herein.

This invention relates to bioreactor systems for the production of tissue prostheses, and to a bioreactor for such a system. Preferred embodiments of the invention relate to bioreactor systems for the production of heart valves (particularly autologous heart valves), although the teachings of the present invention may equally be applied to the production of other body vessels such as veins or arteries.

BACKGROUND OF THE INVENTION

Many thousands of patients are treated every year for heart valve dysfunction. Of these patients, a significant number end up having one or more of their heart valves surgically replaced. In general terms, replacement valves are either xenografts or homografts. Xenografts include mechanical or biological valve prostheses. Homografts include cryo-preserved or glutaraldehyde-fixed explanted valves. Both types of valve have drawbacks.

For example, to avoid thromboembolic complications it is typically necessary for patients fitted with mechanical valve prostheses to be prescribed anticoagulation drugs for life, thereby permanently increasing that patient's risk of haemorrhaging. Infections are a further, often life-threatening complication for the patient. Biological xenografts, for example pig valves treated with glutaraldehyde, can be employed but their tendency to calcify poses a problem.

Homografts, i.e. fixed heart valves isolated from human donors, are relatively resistant to infections, but are nonetheless exogenous tissue which can still cause immune reactions. The availability of homografts tends to be limited, and what's more they also tend to calcify and are therefore subject to considerable degeneration—typically requiring re-operation after 7 to 12 years.

In addition to the disadvantages already described, a further disadvantage is that they are all made of inorganic or fixed organic material and therefore lack the capacity for repair, for reconfiguration or for growth. As a result it is commonplace, in particular for younger patients, to have to undergo a series of operations as they grow up. Aside from the inherent risk associated with any surgical procedure, fusions occurring in the thorax following preceding operations tend to significantly increase the risks associated with each subsequent re-operation.

To alleviate problems such as these it has previously been proposed to "grow" autologous bioengineered prostheses for surgical implantation into patients. Such prostheses, being grown from the patient's own tissue, are less likely to provoke an adverse immune response. Furthermore, as these implants are formed of living tissue, they are able to grow with the patient to such an extent that the need for re-operation (to replace prostheses that have reached the end of their life) is greatly reduced.

Our previous work has proposed an in vitro method whereby an autologous heart valve can be grown in a bioreactor. In this method a biodegradable support is incubated with homologous fibroblasts and/or myofibroblasts to form a connective tissue-like matrix that is then colonized with (typically autologous) endothelial cells. The connective tissue-like matrix is then transferred into a bioreactor for culturing and conditioning of the implant to the flow conditions that it is likely to experience when transplanted into the human body. The scaffold degrades (at least substantially) whilst in the bioreactor, so that at the time of its implantation, the prosthesis is comprised of some biomaterial and preferably autologous cell material that can readily be sewn into the receiving patient's heart. Further details of such prostheses are disclosed in International PCT Publication No. WO 2004/018008, the contents of which are incorporated herein by reference.

FIG. 1 is a schematic representation of a bioreactor system 1 that we have previously proposed for the production and conditioning of heart valves as described above. As depicted, the bioreactor system 1 comprises a bioreactor 3, a reservoir 5 for culture medium, and an eccentric pump 7. An inlet conduit 9 couples an outlet 11 of the reservoir 5 via a non-return valve 13 to an inlet 15 of the bioreactor 3, and an outlet conduit 17 couples an outlet 19 of the bioreactor 3 via a second non-return valve 21 to an inlet 23 of the reservoir 5. As depicted, the reservoir inlet and outlet ports are always submerged in fluid so that the bioreactor 3, inlet and outlet conduits are always substantially free of air. The pump 7 is coupled to the bioreactor 7 via a fluid (typically air) supply line 25, and is operable (as will later be described) to drive fluid into and out of the bioreactor to cause a circulation of culture medium through the system.

The bioreactor is illustrated schematically in more detail in FIG. 2. As shown, the bioreactor 3 comprises an outer casing formed by a bottom section 27, a middle section 29 and a top section 31 bolted together by a series of bolts 33. A resilient membrane 35 is sandwiched between the bottom 27 and middle 29 sections and defines a pumping fluid cavity 37 that is coupled to the pump 7 via inlet/outlet port 39 and fluid line 25 (see FIG. 1). The middle section 29 defines a culture medium inlet chamber 41 that is in fluid communication (by means of a central bore 43) with a nutrient chamber 45 defined by the top section 31.

As depicted, the central bore 43 projects into the nutrient chamber 41 to form a mounting stub 47 onto which mounting ring 49 is mounted. A tissue prosthesis, such as a valve (not shown), can then be fixedly attached to the mounting ring for conditioning in the bioreactor.

In use, the pump 7 is operated to provide a pulsatile flow of fluid through the tissue prosthesis provided in the bioreactor. This pulsatile flow is provided by driving gas (typically air) into and out of the fluid cavity 37 to deform the resilient membrane 35 in an upward (on a pumping stroke) and downward (on a return stroke) direction (as depicted).

During the pumping stroke, gas is pumped into the gas cavity 37 to deform the resilient membrane 35 upwardly. Upward deformation of the resilient membrane drives fluid from the inlet chamber 41 up through the central bore 47, through the tissue prosthesis (not shown) fixedly attached to the mounting ring 49, and out of the top section via outlet port 19. As the membrane 35 moves upwards, the first non-return valve 13 opens to allow fluid to flow from the reservoir outlet port 11 via inlet conduit 9 and into the inlet chamber 41 via inlet port 15. Simultaneously, the second non-return valve 21 opens to allow fluid to flow out of the outlet port 19 and into the reservoir via outlet conduit 17 and reservoir inlet port 23.

The return stroke of the pump 7 draws air out of the gas cavity 37 and deforms the resilient membrane 35 downwardly. Movement of the resilient membrane 35 downwards closes both of the non-return valves and at least substantially prevents fluid flow back through the tissue prosthesis mounted on the mounting ring 49.

As we have previously disclosed, the pump rate should be closely controlled so that the rate of fluid flow through the tissue prosthesis mounted in the bioreactor is slowly increased, principally to avoid damaging the prosthesis, to a point where it mimics that which one might expect to find when the prosthesis is implanted in a patient. This approach provides for a slow conditioning of the prosthesis to the flow rates and pressures that one might expect the prosthesis to experience when implanted in a patient, and as a result renders the prosthesis less likely to failure on eventual implantation into a patient.

Whilst this approach has previously worked well, we have noted that fine control of eccentric pumps is problematic. In particular, we have noted that whilst we can set an eccentric pump to operate at a given speed (and hence theoretically provide a particular output (in terms of liters per minute)), we do not know what the actual pump output is. Furthermore, the nature of the eccentric pump design means that consecutive pumping strokes do not necessarily provide the same output. This problem can be exacerbated at higher pump rates, the effect being that the error in expected output (i.e. the pump output that one would expect for a given pump setting) increases quasi-exponentially as the pumping rate increases. As our prosthesis conditioning process involves operating the pump at indicated rates of up to roughly 5 liters per minute (a relatively high rate) the error between the set pump output and the actual pump output can be considerable, and more importantly liable to fluctuate with each pumping stroke.

A related problem is that whilst it is possible to set the pump to operate at a given indicated rate, we can only infer from this indicated rate the actual rate of culture medium flow through the bioreactor. Given the inaccuracies in pump output, and the fact that we are driving the membrane and not the culture medium, it is likely that the actual rate of culture medium flow is significantly different to that notionally indicated by the setting of the pump. Clearly it would be advantageous for close control of the culture medium flow rate and the conditioning process as a whole for the actual culture medium flow rate to be controllable.

Another problem associated with the bioreactor design we have previously proposed is that it is relatively inconvenient to operate. For example, once a prosthesis has been located in the bioreactor for culturing and conditioning, the bioreactor must be refilled with culture medium. This is done by decoupling the outlet conduit 17 from the second non-return valve 21, and then supplying culture medium (slowly so as to avoid damage to the prosthesis mounted in the bioreactor as might otherwise be caused if the fluid were to be quickly introduced into the chamber) via the inlet 15.

Typically this is done by slowly lifting the reservoir above the bioreactor so that fluid flows under gravity into the bioreactor. The fluid fills the internal voids 41, 45 of the bioreactor until it flows past the second non-return valve 21, and out of the decoupled tubing. At this point the bioreactor is considered to be "filled", and the reservoir is lowered to cut off the gravity flow of fluid into the reactor. The outlet conduit 17 can then be reconnected to the second non-return valve 21, and the system is ready for operation.

A first problem associated with this arrangement is that as it necessarily involves some spillage of culture medium (through the valve 21 on decoupling of the outlet conduit 17), it is relatively messy—and as such not consistent with desirable clean room procedures. A second problem is that as it is necessary to monitor the amount of culture medium in the bioreactor, a spillage of culture medium means that one does not know exactly how much fluid is left to circulate through the bioreactor. A third problem is one of convenience. As the outlet conduit 17 is full of culture medium one needs one hand to close the conduit while one decouples it from the second non-return valve 21 with the other. Without letting go of the outlet conduit one then needs to lift the reservoir to cause the culture medium to flow into the bioreactor.

A further problem associated with the system depicted in FIG. 1 is related to its size. As shown, the system includes a number of components joined by conduits, and as a consequence the footprint of each system is relatively large. In the context of an industrial scale operation, the relatively large size of each system requires a relatively large amount of space, and this space requirement has ramifications for the cost of the production, and ultimately the sales price of the prostheses produced by the process.

BRIEF SUMMARY OF THE INVENTION

It is an aim of the present invention to alleviate some or all of these problems, and to this end a presently preferred embodiment of the present invention provides a bioreactor system comprising: a bioreactor having an input port and an output port, a culture medium reservoir having an input port and an output port, a first conduit coupled between the bioreactor input port and the reservoir output port, a second conduit coupled between the bioreactor output port and the reservoir input port, pump means operable to pump fluid into and draw fluid out of a pumping chamber defined in the bioreactor to generate a pulsatile flow of culture medium through the reservoir and bioreactor via said first and second conduits, one or more flow meters operable to generate flow rate signals representative of the rate of culture medium flow through one or both of said first and second conduits, and control means arranged to receive said flow rate signals from said one or more flow meters and to control the pump means in response to said received flow rate signals to provide a desired rate of culture medium flow.

A further embodiment of the present invention relates to a method of operating a bioreactor system that comprises a bioreactor having an input port and an output port, a reservoir for culture medium having an input port and an output port, a first conduit coupled between the bioreactor input port and the reservoir output port, a second conduit coupled between the bioreactor output port and the reservoir input port, one or more flow meters operable to generate signals representative of the rate of culture medium flow and a pump, the method comprising operating the pump to pump fluid into and draw fluid out of a pumping chamber defined in the bioreactor to generate a pulsatile flow of culture medium through the reservoir and bioreactor via said first and second conduits; generating flow signals representative of the rate of culture medium flow through one or both of said first and second conduits, and controlling the pump to in response to said generated flow signals to provide a desired rate of culture medium flow.

Another embodiment of the present invention provides a bioreactor for culturing and conditioning of tissue prostheses, the bioreactor comprising a plurality of shaped components which when assembled together define: a culture medium reservoir, a pumping chamber split by a movable membrane into a culture medium pumping chamber and a pumping fluid chamber; and a prosthesis mounting chamber, wherein the culture medium pumping chamber is in fluid communication with the reservoir and the prosthesis mounting chamber, and the prosthesis mounting chamber is in fluid communication with the culture medium pumping chamber and the reservoir, the bioreactor further comprising means for limiting circulation of culture medium within the bioreactor to a flow from the reservoir into the pumping chamber, and from the pumping chamber into the reservoir via the prosthesis mounting chamber.

Preferred features and advantages of each of these embodiments are set out in the claims and elsewhere in the following detailed description.

BRIEF DESCRIPTION OF THE DRAWINGS

Preferred embodiments of the present invention will now be described, by way of illustrative example only, with reference to the accompanying drawings, in which.

It should be noted that where directions (such as upwards, downwards, top, bottom etc) are mentioned in the following description they are used only to facilitate understanding of the teachings of the invention, and should not be read as implying any particular orientational limitations to the scope of the invention.

DETAILED DESCRIPTION OF THE INVENTION

As mentioned above, FIGS. 1 and 2 are schematic representations of our previously proposed bioreactor system and bioreactor.

Figure 1:
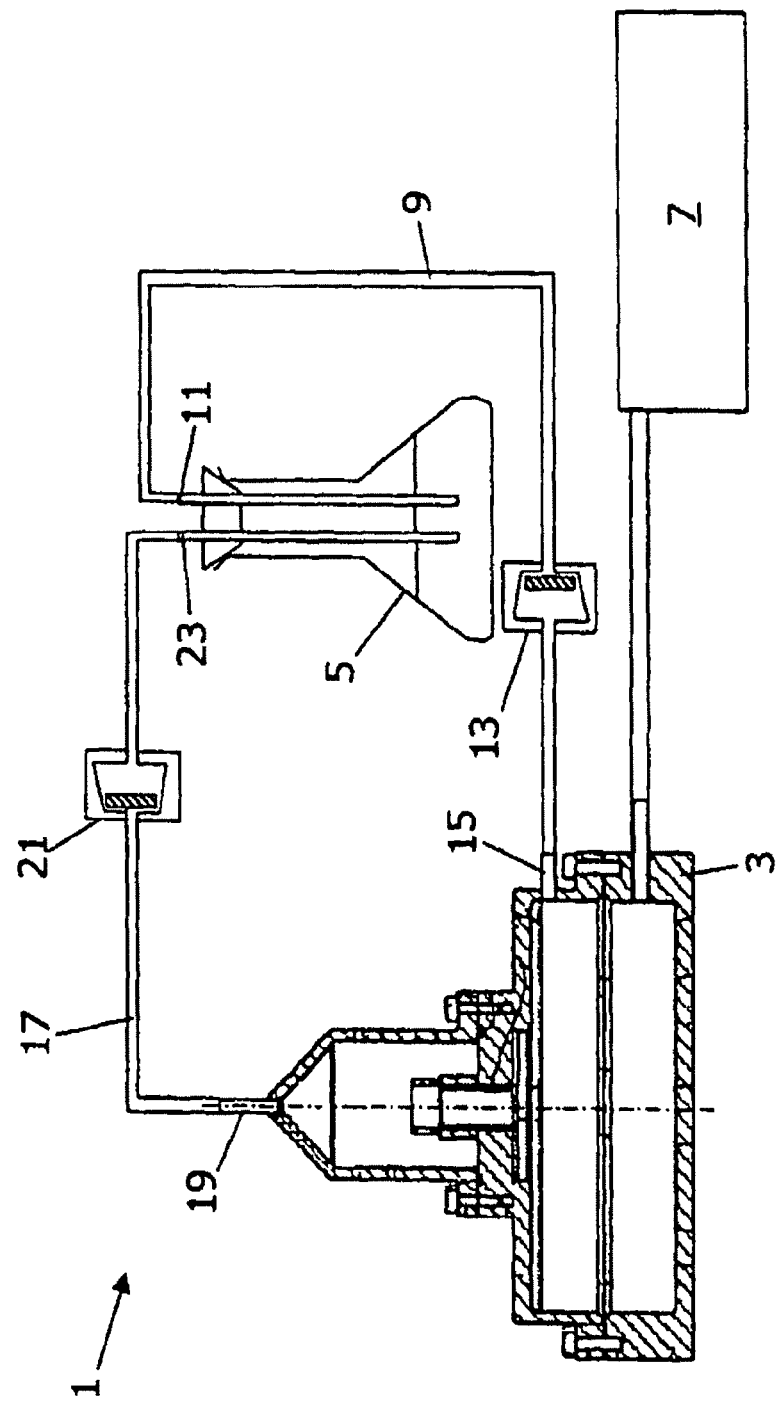
FIG. 1 is a schematic representation of a previously proposed bioreactor system.
Figure 2:
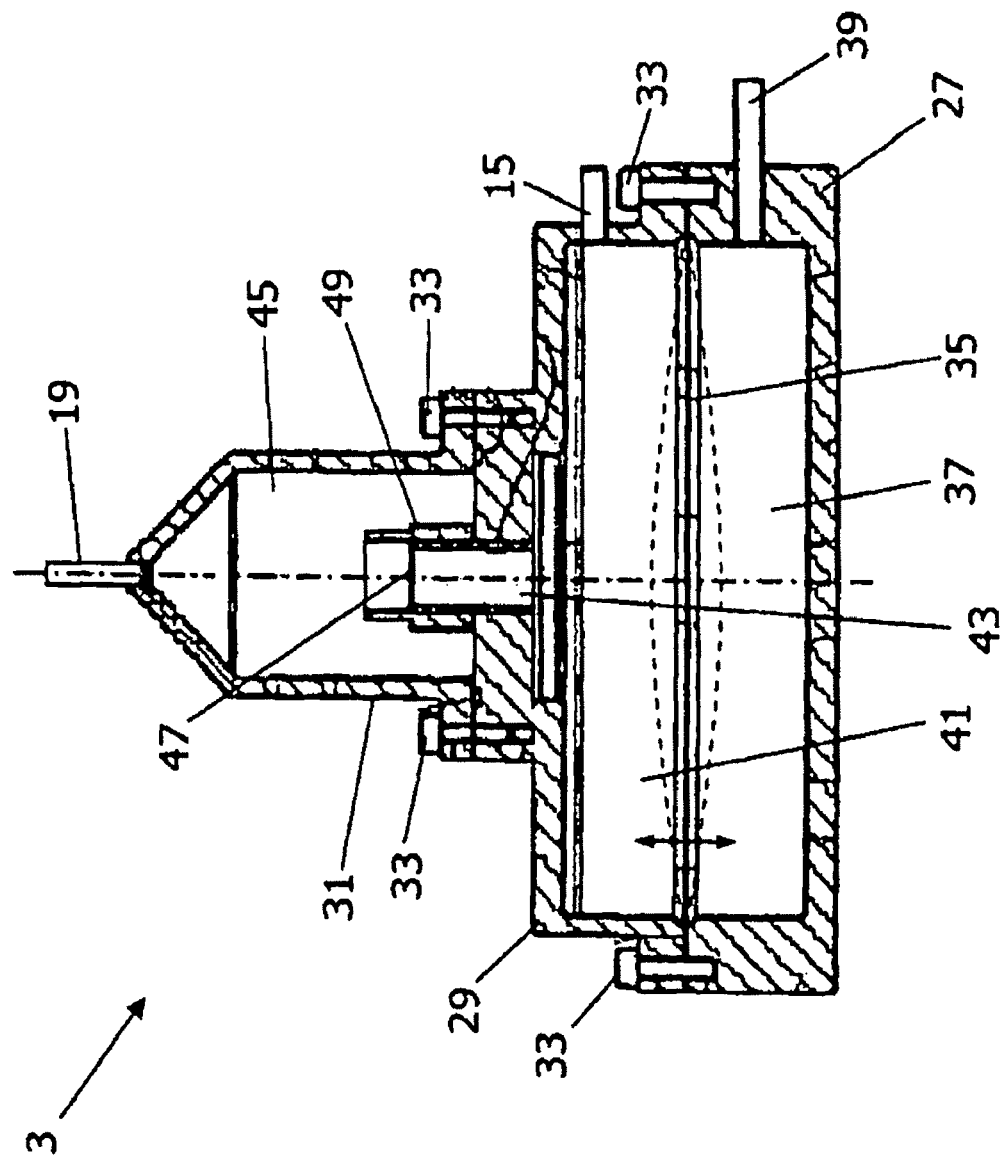
FIG. 2 is a schematic representation of a previously proposed bioreactor.
Figure 3:
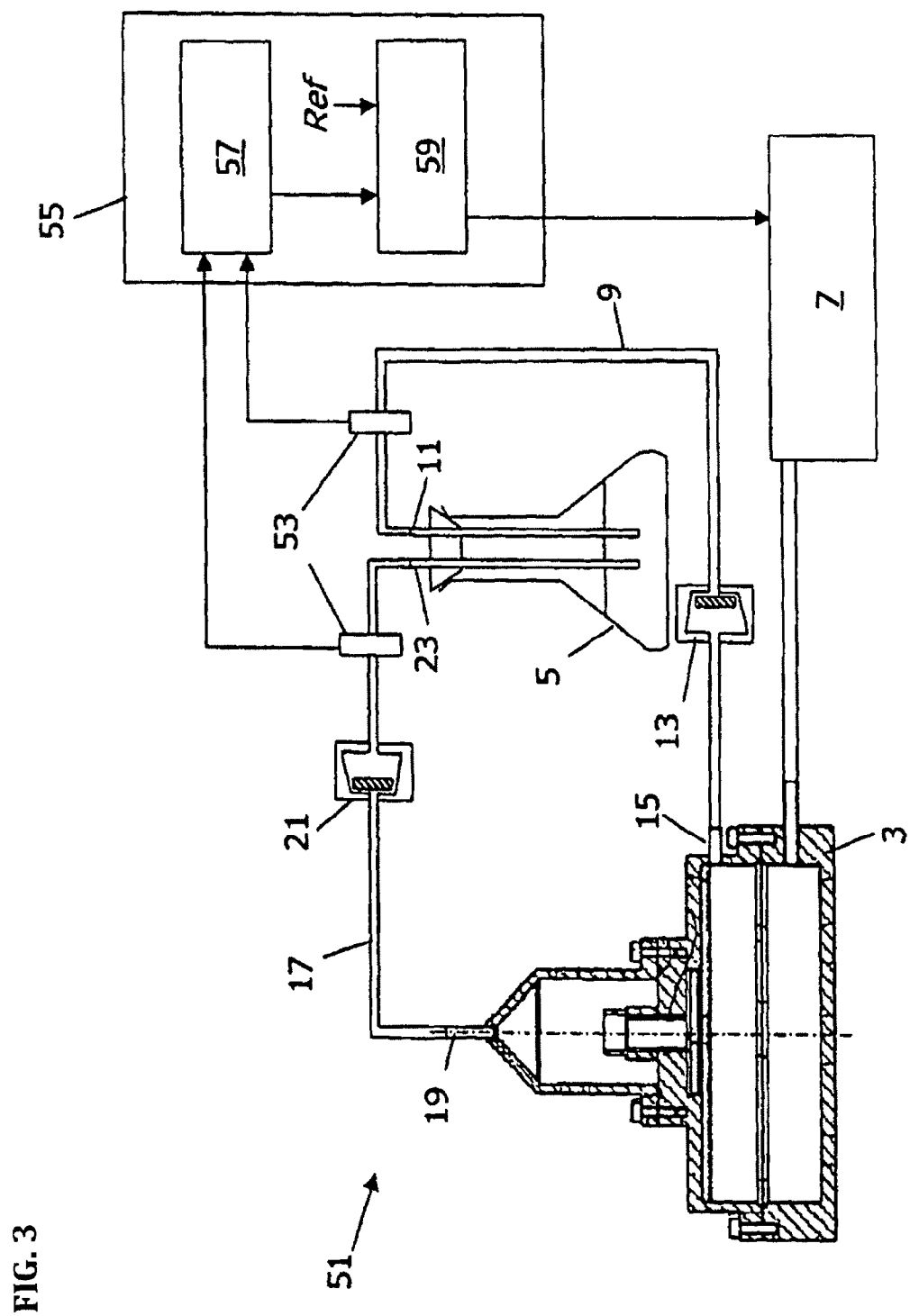
FIG. 3 is a schematic representation of a bioreactor system in accordance with a preferred embodiment of the present invention.

Referring now to FIG. 3, there is shown a bioreactor system 51 which is similar in part to that previously proposed and shown in FIG. 1. For efficacy of description, components with similar functions in the systems depicted in FIGS. 1 and 3 will be referenced by the same reference numerals.

As shown the system 51 according to this embodiment of the invention comprises a bioreactor 3, a reservoir 5 for culture medium, and a pump 7. An inlet conduit 9 couples an outlet 11 of the reservoir 5 via a non-return valve 13 to an inlet 15 of the bioreactor 3, and an outlet conduit 17 couples an outlet 19 of the bioreactor 3 via a second non-return valve 21 to an inlet 23 of the reservoir 5. As depicted, the reservoir inlet and outlet ports are always submerged in fluid so that the bioreactor 3, inlet and outlet conduits are always substantially free of air. The pump 7 is coupled to the bioreactor 7 via a fluid (typically air) supply line 25, and is operable (as described above) to drive fluid into and out of the bioreactor to establish a pulsatile flow of culture medium through the system.

In the preferred arrangement both the inlet and outlet conduits include flow meters 53 that are operable to generate signals representative of the rate of culture medium flow through respective conduits. A controller 55 is arranged to receive the flow rate signals from the flow meters 53, and is coupled to the pump 7 for the control of the pump in response to the signals received.

In a preferred embodiment the controller 55 includes an averaging module 57 that is operable to calculate the average of the two flow rate signals input thereto. The average flow rate signal is then compared by a comparison module 59 with a reference signal (Ref) representative of a desired culture medium flow rate (for example a culture medium flow rate set by an operator or pre-programmed). If the average signal is found to be representative of a flow rate that is less than that which is desired, the pump is controlled to increase the flow rate, for example by increasing the rate of pumping. Similarly, if the average signal is found to be representative of a flow rate that is more than that which is desired, the controller controls the pump to reduce the flow rate, for example by reducing the rate of pumping.

This arrangement is advantageous in that it allows an operator of the system to set a desired flow rate, and leave the system to automatically control the pump operation so that the actual flow rate is at least close to that desired. This differs significantly from systems previously proposed wherein one had no real measure of the rate of culture medium flow. A further advantage of this arrangement is that the controller 55 can be programmed to follow a set flow rate program whereby the flow rate is increased (or otherwise varied) gradually over time to condition a prosthesis mounted in the bioreactor.

Many modifications to this embodiment will be apparent to persons of ordinary skill in the art. For example, as an alternative to providing two flow rate meters, only one meter (on one or other of the conduits) need be provided. In such an arrangement the aforementioned averaging module can be dispensed with.

In a highly preferred implementation, the flow meters are so-called non-invasive flow meters that are designed to measure the rate of medium flow without having to come into contact with the medium. This arrangement is advantageous firstly because it prevents matter such as lubricants in the flow meters from contaminating the culture medium, and secondly because it avoids having to autoclave the flow meters prior to use. As an illustrative example, the flow meters may be ultrasonic non-invasive flow meters—the like of which are readily available from a variety of sources.

The pump 7 may comprise an eccentric pump, as aforementioned, in which case control of the pump is accomplished solely by increasing or decreasing the pumping rate. In a particularly preferred implementation, the pump may instead be a linear pump, and in this instance control of the pump (in response to supplied flow rate signals) may be accomplished by varying the stroke length and/or the pump rate of the pump.

Figure 4:
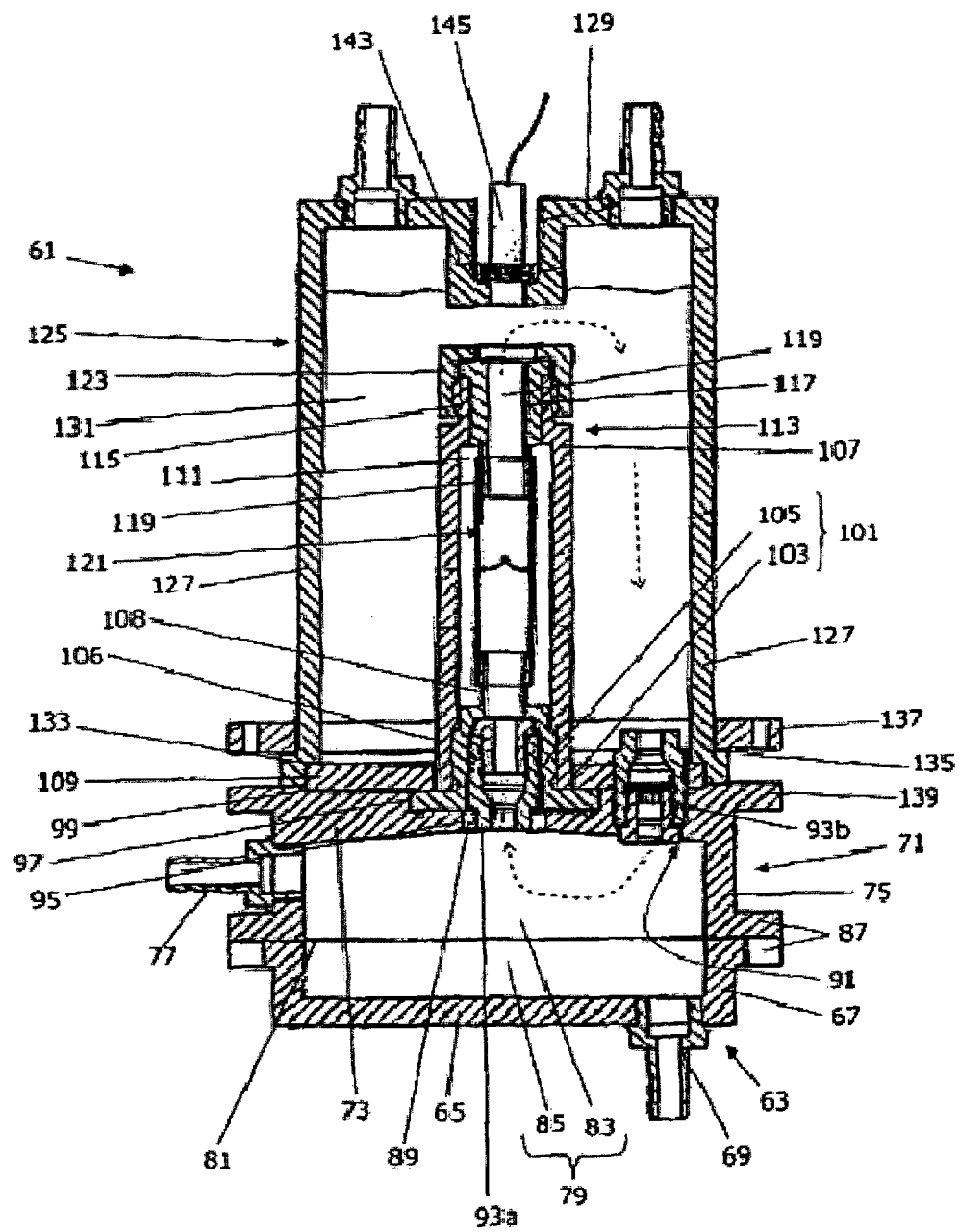
FIG. 4 is a schematic cross-sectional representation of a bioreactor in accordance with a second preferred embodiment of the present invention.

Referring now to FIG. 4, there is shown a schematic of a bioreactor 61 in accordance with a further embodiment of the present invention.

As shown, the bioreactor is comprised of a plurality of shaped components which can be assembled together to define, in a single unitary structure, the bioreactor and reservoir components of the bioreactor system previously proposed. This arrangement has a reduced footprint in comparison with that previously proposed, and is also more convenient to operate.

The bioreactor 61 comprises a dish-shaped base component 63 that includes a generally planar base 65 with an upstanding peripheral wall 67. An inlet/outlet port 69, through which fluid medium can be pumped (as will later be described), is securely received in the base 65 of the base component 63.

The base component 63 mates with a middle component 71 which includes a dished top wall 73 and a depending peripheral wall 75. A culture medium inlet/outlet port 77 that is normally closed (for example by means of a tap (not shown)) in operation of the bioreactor, is securely received in the depending peripheral wall 75.

As shown, the base component 63 and middle component 71 can be assembled together, with the peripheral walls 67, 75 abutting, to define an internal pumping chamber 79 that is divided by a resiliently deformable membrane 81 clamped between the peripheral walls 67, 75 of the base component and middle component into a culture medium pumping chamber 83 and a pumping fluid chamber 85. The peripheral walls of the base component and middle component include lateral flanges 87 through which bolts can be passed to securely fasten the base 63 and middle 71 components together.

The dished top wall 73 of the middle component includes a central bore 89 and an off-centre aperture 91 in which respective non-return valve assemblies 93a, 93b are securely received. The non-return valve assemblies are arranged such that fluid can only flow downwards into the culture medium pumping chamber 83 through the second valve assembly 93b, and can only flow upwards out of the culture medium pumping chamber 83 through the first valve assembly 93a.

The central bore 89 of the dished top wall 73 is stepped to provide a first section 95 of smallest diameter, a second section 97 having a larger diameter than the first, and a third section 99 having a larger diameter than that of the second section 97. The first non-return valve assembly 93a locates within the first section 95 and is secured in place by a retaining formation 101 that locates within the second section 97. The retaining formation 101 comprises a lateral peripheral flange 103 that fits within the second section 97, and an upstanding hollow shroud 105 that fits (preferably snap-fits) over the body of the first non-return valve assembly 93a. The shroud 105 includes a central bore (as depicted) so that culture medium can flow therethrough, and is extended at its uppermost end to provide a first mount 108 for a prosthesis.

A lowermost end 106 of a tubular section 107 locates on the shroud 105 (preferably by means of a push-fit coupling), and the tubular section 107 is held in place by means of a retaining plate 109 which fits thereover and locates in the aforementioned third section 97 of the central bore 89. The retaining plate also includes an off-centre aperture that is sized to fit over the second non-return valve assembly 93b such that the second valve assembly 93b is securely located in the aforementioned off-centre aperture 91 in the dished top wall 73 of the middle component 71.

The tubular section 107 includes an internal bore which forms a prosthesis mounting chamber 111. The uppermost end 113 of the tubular section narrows to provide an upstanding shoulder 115 in which a mounting plug 117 having a central bore 119 is received. The mounting plug 117 is extended at its lowermost end to provide a second mount 119 for a prosthesis 121. In the particular example illustrated, the prosthesis is a valve.

The mounting plug 117 is held in place with respect to the tubular section 107 by means of a cap 123 which includes a central aperture (to permit culture medium flow therethrough) and a peripheral wall that fits securely, preferably snap fits, on the upstanding shoulder 115 of the tubular section 107.

A hollow top component 125 having an open end defined by a peripheral wall 127 depending from a base 129, fits over the tubular section 107 and defines an internal void which forms a culture medium reservoir 131. The peripheral wall abuts against the top wall of the middle component 71, and includes an internal step 133 which locates on the retaining plate 109, and an external step 135. The external step 135 forms a ledge against which a retaining ring 137 abuts, and the retaining ring 137 is securely coupled (e.g. bolted) to a peripheral flange 139 of the middle section 71 to render the bioreactor fluid tight. A seal (such as an o-ring type seal for example) may be provided between the peripheral wall and the top wall of the middle component 71 if required to render the bioreactor fluid tight.

The base 129 of the top component includes, in this example, two off-centre apertures in which inlet couplings 141 are provided. These couplings are normally closed during operation of the bioreactor, and are provided only for convenience in the event that something needs to be added to the bioreactor once it has been set to operate. The apertures and couplings 141 need not be provided.

The base 129 also includes an optional central depression 143 configured to align with the tubular section 107. In this instance a video camera 145 has been mounted in the base of the depression so that operation of the prosthetic valve 121 can be visually monitored during the culturing and conditioning process.

As will be apparent from the foregoing, the bioreactor of this embodiment can be completely disassembled into its constituent parts for sterilization prior to use. It is also the case that the bioreactor need only be connected to a pump, and as such has a significantly smaller footprint than the bioreactor and reservoir components of the system previously proposed. As described below, it is also the case that the bioreactor of this embodiment is significantly more convenient to operate than that previously proposed.

Prior to describing how the bioreactor operates, it is appropriate at this juncture to devote a few paragraphs to a brief description of the prostheses that can be conditioned in the bioreactor of this embodiment, or indeed in that of the previous embodiment.

As mentioned briefly above, tissue prostheses for culturing and conditioning in bioreactors of the types previously described essentially comprise a scaffold of biodegradable material which is colonised with homologous fibroblasts and/or myofibroblasts to form a connective tissue matrix. This tissue matrix is then colonised with (typically autologous) endothelial cells and conditioned in the bioreactor, during which time the scaffold degrades to leave a prosthesis which is at least substantially of, preferably autologous, cell material that can readily be sewn into the receiving patient.

In the case of a valve prosthesis, the prosthesis may include only the valve component (i.e. only the moveable leaflets that restrict backflow of fluid when implanted in a patient). Alternatively, the valve scaffold component may be fixed within a tubular vessel scaffold component so that the surgeon does not have to implant a valve into an existing vessel or organ (a relatively difficult task), but can simply replace a section of vessel with the prosthesis.

In the former case, the valve prosthesis is mounted in a tube (for example a silicone tube) prior to conditioning of the prosthesis in the bioreactor, and the tube can be mounted in the bioreactor (by push fitting respective ends of the tube onto the first and second mounts respectively). In the latter case the prosthesis can either be directly mounted into the bioreactor for conditioning (by push fitting respective ends of the tubular scaffold onto the first and second mounts), or can be coupled (for example by suturing or glue) at either end to short sections of tubing (e.g. silicone tubing) which can then be mounted (for example, push fitted) on the first and second mounts respectively.

Hereafter, the prosthesis will be described generically as comprising a valve component and a tubular component (it being understood that in circumstances where the tubular component is a silicone tube, the valve will first be removed from the tube before implantation in a patient).

Once the bioreactor of this embodiment has been disassembled and sterilized, the first step of the reassembly process is to assemble the base 63 and middle 71 components by arranging the resiliently deformable membrane 81 in between the peripheral walls 67, 75 of the base and middle components and then bolting the flanges 87 together to secure the middle component to the base. Once this has been done the inlet/outlet ports 69, 77 can be fitted to the base and middle components, and the second non-return valve assembly 93b can be located in the off-centre aperture 91 in the top wall 73 of the middle component 71.

The next step in the reassembly process is to push fit the second mount 119 into an end of the tubular prosthesis component (care being taken to ensure, in circumstance where the prosthesis is a valve, that the second mount 119 is pushed into the end of the tubular component that the valve component opens towards when fluid flows through the valve).

Once the tubular prosthesis component has been fitted to the second mount 119, the prosthesis can be inserted into the internal void of the tubular section 107 that forms the prosthesis mounting chamber 111. The cap 123 can then be snap-fitted onto the tubular section 107 to hold the second mount (and hence the one end of the tubular prosthesis component) in a fixed position with respect to the tubular section 107.

The next stage in the assembly process is to fit the first non-return valve assembly 93a into the retaining formation 101 such that the first mount 108 projects from the hollow shroud 105. The shroud 105 and projecting first mount 108 are then pushed into the open end of the tubular component 107 so that the first mount fits into the free end of the tubular prosthesis, and the tubular component 107 snap-fits on the shroud 105.

Next, the tubular section is fitted onto the middle component 71 so that the lateral flange 103 of the retaining formation 101 locates in the second section 97 of the central bore 89 of the middle component 71. The retaining plate 109 can then be fitted over the tubular component 107 and second non-return valve 93b, and located in the third section 99 of the central bore 89.

The final steps in the assembly process comprise fitting the top component 125 over the tubular component 107 so that the step 133 locates on the retaining plate 109, following which the retaining ring 137 is securely bolted to the peripheral flange 139 of the middle section 71 to render the bioreactor fluid tight.

Once the bioreactor has been assembled with the prosthesis located within the prosthesis mounting chamber 111, the bioreactor can be filled with culture medium. This is done by coupling an external reservoir to the culture medium inlet/outlet port 77, opening the tap (not shown) and slowly supplying culture medium at a small positive pressure to the inlet/outlet port. This can be accomplished by physically lifting the external reservoir so that the fluid therein flows under gravity into the bioreactor.

As culture medium flows into the bioreactor it fills the culture medium pumping chamber 83, opens the first non-return valve assembly 93a (by virtue of the force exerted by the pressurised fluid on the valve) and slowly fills the internal void 111 of the tubular component 107. Once the culture medium has filled the internal void, it spills out of the cap 123 and fills the reservoir 131 until, as depicted, the tubular component is completely immersed in culture medium. At this point the tap can be closed, and the pumping fluid inlet/outlet port 69 can be connected to a pump (not shown), for example an eccentric or linear pump. Draining of culture medium from the bioreactor (for example when the conditioning process has been completed) can be accomplished simply by opening the tap (not shown) attached to the culture medium inlet/outlet port.

Operating the pump to drive pumping fluid, typically air, into the pumping fluid chamber 85 causes the resilient membrane 81 to deform upwardly from the depicted equilibrium position and pressurise the fluid in the culture medium chamber 85. The pressurised culture medium opens the first non-return valve 93a (whilst preventing the second non-return valve 93b from opening) and flows through the prosthesis (opening the valve component if provided) and out of the cap 123 into the reservoir 131.

On the return stroke of the pump, pumping fluid is drawn out of the pumping fluid chamber 85 and the resilient membrane deforms downwardly from the depicted equilibrium position. Downward deformation of the membrane causes a reduction in the pressure of culture medium in the culture medium pumping chamber 83 which draws the first non-return valve 93a closed, and opens the second non-return valve 93b to allow culture medium to flow from the reservoir 131 into the pumping fluid chamber 83. Continued operation of the pump reciprocates the resilient membrane 81 about the depicted equilibrium position and that reciprocation establishes a pulsatile flow, as aforementioned, through the prosthesis to condition the prosthesis prior to implantation.

As will be appreciated from the foregoing, the bioreactor of this embodiment is significantly more convenient than that previously proposed. In particular, by integrating the bioreactor and reservoir of the system previously proposed in a single unitary structure the bioreactor can easily be filled and emptied without spillage of culture medium and without having to decouple and recouple the reservoir from the bioreactor whilst the bioreactor is filled. It is also the case that the bioreactor of this embodiment is significantly more compact than the bioreactor/reservoir combination previously proposed.

Whilst various preferred embodiments of the invention have been described above in detail, it will be appreciated that modifications can be made to the particular embodiments described without departing from the scope of the present invention. For example, whilst the controller has been described above in functional terms, persons skilled in the art will readily be able to implement that functionality by way of analogue or digital, or indeed a combination of analogue and digital, electronic components.

It should also be noted that whilst particular combinations of features herein described have been explicitly enumerated in the accompanying claims, the scope of the invention is not limited to those particular combinations but instead extends to any combination or permutation of features herein described.

The invention claimed is:

1. A bioreactor system for the production of tissue prostheses, the system comprising:
   a bioreactor having an input port and an output port,
   a culture medium reservoir having an input port and an output port,
   a first conduit coupled between said bioreactor input port and said culture medium reservoir output port,
   a second conduit coupled between said bioreactor output port and said culture medium reservoir input port,
   a pump operable to pump fluid into and draw fluid out of a pumping chamber defined in said bioreactor to generate a pulsatile flow of culture medium through said culture medium reservoir and bioreactor via said first and second conduits,
   one or more flow meters operable to generate flow rate signals representative of the rate of culture medium flow through one or both of said first and second conduits,
   a controller arranged to receive said flow rate signals from said one or more flow meters and to control a pump in response to said received flow rate signals to provide a desired rate of culture medium flow, wherein said bioreactor comprises a plurality of shaped components which when assembled together define:

said pumping chamber,
  wherein said pumping chamber is split by a movable resilient membrane into a culture medium pumping chamber and a pumping fluid chamber; and
  wherein said pumping chamber is defined by a hollow base component and a
  hollow middle component,
said culture medium reservoir,
  wherein said culture medium reservoir is defined by a hollow top component mounted on a wall of said hollow middle component,
a prosthesis mounting chamber,
  wherein said culture medium pumping chamber is in fluid communication with said culture medium reservoir and said prosthesis mounting chamber, and said prosthesis mounting chamber is in fluid communication with said culture medium pumping chamber and said culture medium reservoir,
said bioreactor further comprising:
a first non-return valve provided in said wall of said hollow middle component for limiting circulation of culture medium within said bioreactor to a flow from said culture medium reservoir to said pumping chamber, and
a second non-return valve for limiting circulation of culture medium within said bioreactor to a flow from said pumping chamber to said culture medium reservoir via the prosthesis mounting chamber,
  wherein said prosthesis mounting chamber is located within said culture medium reservoir.

2. The bioreactor system according to claim 1, wherein said one or more flow meters comprise non-invasive flow meters operable to generate signals representative of a rate of culture medium flow without contacting said culture medium.

3. The bioreactor system according to claim 1, wherein said pump comprises a linear pump.

4. The bioreactor system according to claim 3, wherein said controller is operable to control one or both of the rate of pump operation and the pump stroke length.

5. The bioreactor system according to claim 1, wherein the movable resilient membrane is clamped between peripheral walls of said base and middle components to define said pumping chamber on a first side of said membrane, and a culture medium chamber on a second side of said membrane into which culture medium is fed from said culture medium reservoir by means of said bioreactor inlet.

6. The bioreactor system according to claim 5, comprising a top component mounted on said middle component and including said bioreactor outlet port, said middle component being in fluid communication with said top component by means of a port provided in a wall of said middle component.

7. The bioreactor system according to claim 6, wherein said port between said middle and top components comprises a prosthesis mount on which a prosthesis may be mounted for conditioning.

8. The bioreactor system according to claim 1, wherein said bioreactor can be completely disassembled for autoclaving.

9. The bioreactor system according to claim 1, wherein said prosthesis mounting chamber comprises a hollow tubular body, a top cap assembly and a bottom cap assembly,
  each of said top and bottom cap assemblies includes a bore such that culture medium can flow into said prosthesis mounting chamber by means of said bottom cap assembly bore, through said hollow tubular body and out of said prosthesis mounting chamber by means of said top cap assembly bore.

10. The bioreactor system according to claim 9, wherein said prosthesis mounting chamber comprises first and second mounts on which respective ends of said prosthesis may be fitted for conditioning.

11. The bioreactor system according to claim 10, wherein said first and second mounts comprise tubular projections from respective components of said top and bottom cap assemblies, the projections extending into said hollow tubular body on fitting of said cap assemblies to said hollow tubular body.

12. The bioreactor system according to claim 9, wherein said bottom cap assembly is mounted on a wall of said hollow middle component, said wall including an aperture to permit fluid communication between said culture medium pumping chamber and said prosthesis mounting chamber.

13. The bioreactor system according to claim 9, wherein said culture medium reservoir is in fluid communication with said prosthesis mounting chamber by means of said top cap assembly bore in said prosthesis top cap assembly, and in fluid communication with said culture medium pumping chamber by means of a second aperture provided in said middle component wall.

14. A method of operating a bioreactor system that comprises:
  providing the bioreactor system of claim 1;
    operating said pump to pump fluid into and draw fluid out of a pumping chamber defined in said bioreactor to generate a pulsatile flow of culture medium through said culture medium reservoir and bioreactor via said first and second conduits;
  generating flow signals representative of the rate of culture medium flow through one or both of said first and second conduits, and
  controlling said pump in response to said generated flow signals to provide a desired rate of culture medium flow.

* * * * *